US006265191B1

(12) United States Patent
Mizusawa et al.

(10) Patent No.: US 6,265,191 B1
(45) Date of Patent: Jul. 24, 2001

(54) IMMOBILIZATION OF PSEUDOMONAS LIPASE ON SURFACES FOR OIL REMOVAL

(75) Inventors: Eugene A. Mizusawa, Castro Valley; Susan A. Anderson, Menlo Park; Maha Y. El-Sayed, Fremont; Daniel R. Leiske, Livermore; Richard J. Wiersema, Tracy; Chihae Yang, Pleasanton, all of CA (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 08/110,341

(22) Filed: Aug. 20, 1993

Related U.S. Application Data

(63) Continuation of application No. 07/583,225, filed on Sep. 14, 1990, now abandoned.

(51) Int. Cl.[7] .......... C12N 11/02; C12N 11/10; C12N 9/20; D06M 16/00

(52) U.S. Cl. .......... 435/177; 435/134; 435/178; 435/198; 435/263; 435/264; 435/877

(58) Field of Search .......... 435/134, 177, 435/178, 198, 263, 264, 877

(56) References Cited

U.S. PATENT DOCUMENTS

| | | | |
|---|---|---|---|
| 3,858,854 | 1/1975 | Win et al. | 252/89 |
| 4,006,059 | 2/1977 | Butler | 435/126 |
| 4,307,151 | 12/1991 | Yamauchi et al. | 428/373 |
| 4,472,503 | 9/1984 | Matsuo et al. | 435/179 X |
| 4,703,872 | 11/1987 | Cornette et al. | 222/158 |
| 4,707,291 | 11/1987 | Thom et al. | 252/174.12 |
| 4,909,962 | 3/1990 | Clark | 252/547 |

FOREIGN PATENT DOCUMENTS

| | | |
|---|---|---|
| 0206390 | 12/1986 | (EP) . |
| 0253487 | 1/1988 | (EP) . |
| 0268456 | 5/1988 | (EP) . |
| 0375102 | 6/1989 | (EP) . |
| 1442418 | 12/1973 | (GB) . |
| 8901032 | 7/1988 | (WO) . |
| 88-09367 | 12/1988 | (WO) . |

OTHER PUBLICATIONS

Ettinger, *Biochemistry*, (1987) 26:7883–7892.

*Primary Examiner*—David M. Naff
(74) *Attorney, Agent, or Firm*—Coudert Brothers

(57) ABSTRACT

Lipase is immobilized on surfaces to facilitate oil removal from the surfaces and to alter wettability of the surfaces. The lipase is isolatable from a Pseudomonas organism such as *Pseudomonas putida* ATCC 53552 or from an organism expressing a coding region found in or cloned from the Pseudomonas. A particularly preferred lipase has a molecular weight of about 30 to 35 kd and is resolvable as a single band by SDS gel electrophoresis. Lipase sorbed on fabric forms a fabric-lipase complex for oil stain removal. The lipase may be sorbed on fabric before or after an oil stain, and the lipase is active to hydrolyze an oil stain on dry fabric or fabric in laundering solutions. The sorbed lipase has enhanced stability to denaturation by surfactants and to heat deactivation, is resistant to removal from fabric during laundering, retains substantial activity after drying fabric at an elevated temperature, and retains activity during fabric storage or wear. Redeposition of oil and oil hydrolysis by-products during laundering of fabric is retarded by the lipase. Oil hydrolysis by-products are removable during laundering of fabric at a basic pH or in the presence of a surfactant.

22 Claims, 3 Drawing Sheets

IMMOBILIZATION OF PSEUDOMONAS LIPASE ON SURFACES FOR OIL REMOVAL

This is a continuation of application Ser. No. 07/583,225, filed Sep. 14, 1990.

FIELD OF THE INVENTION

The present invention relates to the field of use of lipases in laundry applications. More broadly, it relates to modification of surfaces such as for oil stain removal, improved wettability and anti-redeposition. More particularly, it relates to formation of hydrolase-fabric complexes which are stable and hydrolytically active during laundering, drying and use, and provide increased oil stain removal, wettability and anti-redeposition properties.

BACKGROUND OF THE INVENTION

Lipases are enzymes naturally produced by a wide variety of living organisms from microbes to higher eukaryotes. Fatty acids undergoing oxidation in tissues of higher animals must be in free form (that is, non-esterified) before they can undergo activation and oxidation. Thus, intracellular lipases function to hydrolyze the triacylglycerols to yield free fatty acids and glycerol. Enzymes useful in the present invention will be referred to as “lipases”, but include enzymes described as being a “hydrolase” or “cutinase”, as well as a “lipase”, because the useful enzymes form hydrolysis by-products from oil substrates. All three terms and enzymes are contemplated and included by the use of the term “lipase” herein.

Bacterial lipases are classically defined as glycerolester-hydrolases (EC 3.1.1.3) since they are polypeptides capable of cleaving ester bonds. They have a high affinity for interfaces, a characteristic which separates them from other enzymes such as proteases and esterases.

Cutinases are esterases that catalyze the hydrolysis of cutin. For example, cutinase allows fungi to penetrate through the cutin barrier into the host plant during the initial stages of a fungal infection. The primary structures of several cutinases have been compared and shown to be strongly conserved. Ettinger, *Biochemistry.* 26, pp. 7883–7892 (1987). Sebastian et al., *Arch. Biochem. Biophys.,* 263 (1), pp. 77–85 (1988) have recently found production of cutinase to be induced by cutin in a fluorescent *P. putida* strain. This cutinase catalyzed hydrolysis of p-nitrophenyl esters of $C_4$–$C_{16}$ fatty acids.

Because of this ability, lipases have long been considered as potential components in detergent compositions, and lipases obtained from certain Pseudomonas or Chromobacter microorganisms have been disclosed as useful in detergent compositions: Thom et al., U.S. Pat. No. 4,707,291, issued Nov. 17, 1987 and Wiersema et al., European Patent Application 253,487, published Jan. 20, 1988. However, although lipases hydrolyze oil in solutions simulating laundry wash compositions, they have not proven to be very effective in removing oil stains from fabrics.

PCT application WO 88/09367 suggests the use of one of the lipases employed in the present invention in laundry applications. However, the method of use suggested merely comprises conventional use in laundry solutions or cleaning compositions. This lipase, so used by conventional methods, is no more effective than other lipases in removing oil stains from fabrics. Therefore, a need remains for effective utilization for the potential of lipases for removing oil stains in laundry applications.

Fabric treatments with non-enzyme compounds are known to alter the properties of fabric surfaces. For example, paralleling the development of durable-press and wash/wear fabrics, has been work on imparting oil and water repellency to fabrics. A widely used treatment utilizes a fluorochemical (sold by Minnesota Mining and Manufacturing Company under the mark Scotchgard) and another composition used for such fabric treatment is sold by E.I. du Pont de Nemours & Co. under the trademark Zepel. But oil and water repellant treated fabric have posed difficulties in removing stains by laundering, due to the fact that these repellant treatments make the fabric hydrophobic, and the oils forced onto such fabrics (particularly clothing at collar and cuffs) therefore are difficult to remove. One approach to this problem has been to treat the fabrics with soil release polymers. However, a need remains for imparting improved oil stain removal properties to surfaces, and particularly to fabrics exposed to significant oil staining, such as table cloths, aprons and clothing at body contact points such as collars and cuffs.

The use of lipases and/or cutinases in imparting oil hydrolysis activity during storage or wear has not been previously recognized.

When soil is released from fabric during laundering there is a further problem of redeposition of the oily soil on the previously cleaned fabric. This problem is well recognized. U.S. Pat. No. 4,909,962, issued Mar. 20, 1990, inventor Clark, attributes the redeposition of oily soil, in part, to phase separation (at least in the case of a pre-spotting composition when diluted with water in the wash bath). U.S. Pat. No. 4,919,854, issued Apr. 24, 1990, inventors Vogt et al., discloses detergent and cleaning preparations which include redeposition inhibitors described as water-soluble, generally organic, colloids (e.g. polymeric carboxylic acids and gelatin).

SUMMARY OF THE INVENTION

The present invention provides a novel use of the oil hydrolyzing potential of lipases for removing oil stains from fabrics more effectively than prior art attempts to utilize lipases for laundry cleaning applications.

In one aspect of the present invention, a method for modifying surfaces is provided to facilitate oil removal therefrom and comprises selecting a surface to be modified and then immobilizing (by chemical or physical means) an lipase onto the surface by forming a surface-lipase complex. The immobilized lipase is isolatable from Pseudomonas organisms. Suitable enzymes are lipases that are isolated from an organism expressing a coding region found in or cloned from *P. putida* ATCC 53552 or P. sp., more preferably from the *putida* species. A particularly preferred lipase is isolated with a molecular weight of about 30,000 daltons and is resolvable as a single band by SDS gel electrophoresis. The surfaces on which the enzyme is immobilized can be solid (e.g. glass) or can be fabrics (natural, synthetic, or metallic, woven or non-woven).

In another aspect of the present invention, a fabric is provided that is treated to have improved oil stain removal properties. The treated fabric has a lipase immobilized on the surface, forming a fabric-lipase complex. The fabric-lipase complex has substantial hydrolysis activity for oil stains during both subsequent use and laundering, and is resistant to removal during such use in laundering. Thus, although initial use of even the preferred lipases will not be effective for oil stain removal, the fabric-lipase-complex is effective for oil stain removal. The preferable lipase used to form the fabric-hydrolase complex is isolated from *Pseudomonas putida* ATCC 53552, including modifications such as mutants or clones.

In yet another aspect of the present invention, a fabric treating composition, useful to improve oil stain removal of fabrics, comprises a solid or gelled carrier and the lipase described above. The lipase is dispersed in the carrier and can be applied to fabric, and once applied, the lipase sorbs and forms the fabric-lipase complexes.

Fabric having improved oil stain removal properties in accordance with the present invention can be repeatedly laundered without effective loss of such preparation because the lipase used is immobilized to the fabric, resists removal during laundering, and has substantial hydrolysis activity for oil stains on the fabric in both air and laundering solutions. The inventive treatments can be used to treat fabrics either before or after exposure to oily stains. The fabrics so treated need not be immediately laundered because the fabric-lipase complexes are hydrolytically active even on dry fabric in ambient air.

Other applications of the ability for the immobilized lipase to modify surfaces include uses to alter the wettability of the surface on which the lipase is sorbed. Thus, for example, solid plastic or glass surfaces having surface modifications in accordance with the invention may facilitate clog removal in plumbing, cleaning of windows, and other uses.

Other objects and advantages of the present invention will become apparent to persons skilled in the art upon reading the following description.

DETAILED DESCRIPTION OF THE PREFERRED EMBODIMENTS

Broadly viewed, the invention is a method for modifying surfaces by forming a lipase complex with the surface. One application of primary intent is to facilitate oil removal from or by a modified fabric surface. By "oil removal" is meant removal of oil which is deposited on the surface either before or after such surface modification, as well as the property of preventing or retarding redeposition of oil on the fabric such as during laundering. Surfaces that can be modified in accordance with the invention include glass, plastic, and metal solids as well as fabrics. Particularly preferred embodiments of the invention pertain to fabrics.

Thus, fabric treating compositions of the invention are useful to treat a wide variety of natural, synthetic or metallic fabrics whether viewed as textiles or woven or non-woven cloths. For example, among the different materials that have been treated in accordance with the invention so as to have sorbed enzyme on surfaces exposable to oils have been nylon, polycotton, polyester, woven polyester, double knit polyester, silk, vinyl, cotton flannel, rayon velvet, acrylic felt, wool blend (polyester/wool), synthetic blend (polyester/polyurethane), as well as pot cleaner materials such as cellulose sponge, nylon and stainless steel scrubbers and copper cloth.

The surfaces that have been treated in accordance with the invention can already be stained by (or carrying) oil before an enzyme-fabric complex is formed or the complex can be formed before such exposure. Examples of embodiments useful for the former applications include pre-wash liquid or gelled compositions that can be sprayed or directly applied to specific areas of oily stains. The garments or linens can then be stored in a laundry hamper, for example, and laundered in the normal course of a household's routine because degradation of the oily stain into hydrolysis by-products will be occurring during storage. Alternatively, fabric may be pretreated before use to convey improved oil stain removal properties.

Surfaces are modified in accordance with this invention by sorbing a lipase onto the surface. The sorbed lipase is isolatable from a Pseudomonas organism.

The suitable lipases can be viewed as glycerol ester hydrolases and are isolatable from certain Pseudomonas strains or from genetic modifications such as mutants or clones thereof. The particular Pseudomonas strains of interest are P. sp. and *P. putida* ATCC 53552, deposited with the American Type Culture Collection, 12301 Parklawn Drive, Rockville, Md. 20852, on Oct. 15, 1986. It should be understood that the gene expressing the particular lipase of interest can be cloned into another organism, such as *E. coli* and *B. subtilis,* for higher levels of expression.

Figure 1:
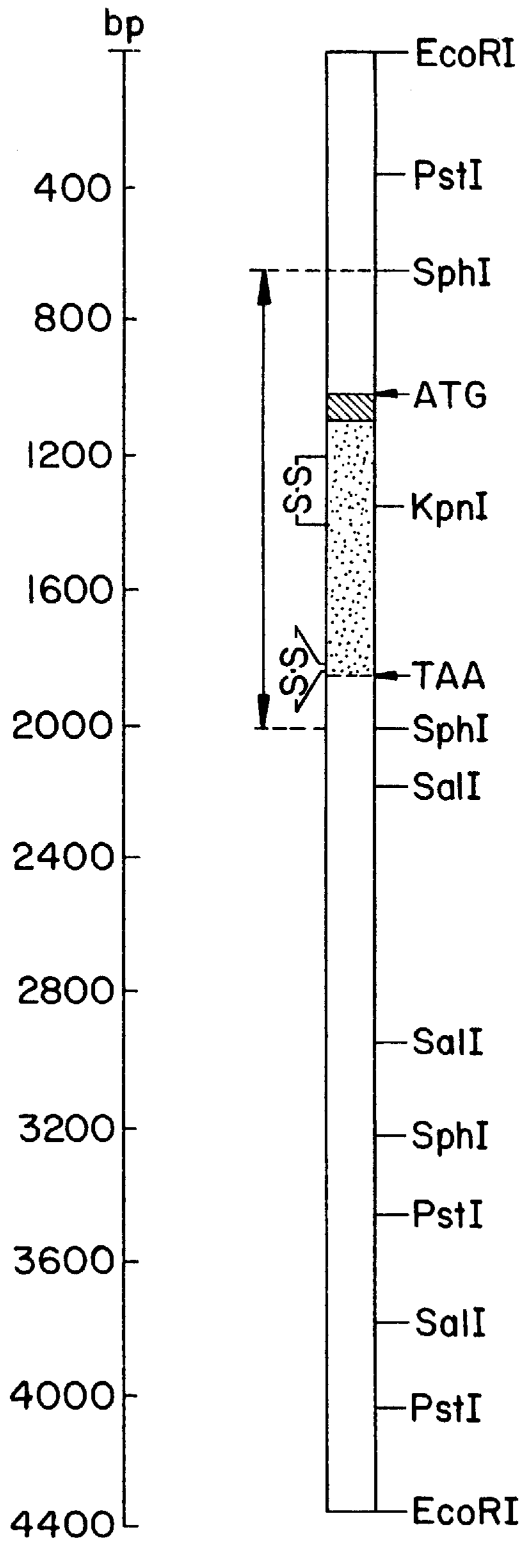
FIG. 1 of this reference is a map of the 4.3kb *E. coli* fragment of a plasmid designated PSNE4, for a lipase useful in the present invention.

The previously noted European Patent Application 253,487 of Wiersema et al. more fully describes the amino acid sequence of a specific suitable enzyme isolatable from the *P. putida* strain and further describes the cloning and expression of the gene coding for this enzyme. FIG. 1 of this reference is a map of the 4.3 kb *E. coli* fragment of a plasmid designated PSNE4 where the stippled region indicates the coding region (codons +1 to +258) for the mature polypeptide designated Lipase 1, which has a molecular weight of about 30,000 daltons and is resolvable as a single band by SDS gel electrophoresis. This EPA 253,487 is incorporated by reference, but for convenience the amino acid sequence of the specific enzyme ("Lipase 1") isolated from the *P. putida* strain is set out as follows:

Suitable enzymes can be modified with respect to the said amino acid primary structure.

Modifications preferably will be wherein the modified enzymes have an amino acid sequence substantially corresponding to the just-described lipase isolatable from *P. putida* ATCC 53552, but differing therefrom within certain parameters. Such preferred modifications are where there is at least one amino acid change occurring within (i) about 15 Å of serine 126, aspartic acid 176 or histidine 206 when the modified enzyme is in crystallized form or (ii) within about 6 amino acids of the primary structure on either side of serine 126, aspartic acid 176 or histidine 206. Such suitable modifications are as described in co-pending U.S. patent application Ser. No. 286,353, filed Dec. 19, 1988, now U.S. Pat. No. 5,108,457, entitled "Enzymatic Peroxyacid Bleaching System with Modified Enzyme", inventors Poulose and Anderson, which is incorporated herein by reference and is of common assignment herewith.

It is found that conventional initial washing with lipases, including the preferred lipases of the present invention, provides virtually no benefit over washing in the absence of lipase. The present invention nevertheless provides a method of employing lipases for effective removal of oil stains from fabric by utilizing a first wash cycle to form a fabric-lipase complex, which remains active through subsequent drying and provides effective oil removal in subsequent wash cycles. An example of this is shown in Table 1 where no stain removal occurs in the first wash cycle, but does occur in subsequent cycles. Polycotton fabric swatches (65/35) were stained with triolein (5% by weight) and washed three times with two lipases of the invention. Table 1 summarizes the data of this study.

TABLE 1

| | % Oil Stain Removal | | |
|---|---|---|---|
| | 1st Cycle | 2nd Cycle | 3rd Cycle |
| Lipase cloned from *P. putida* | | | |
| 0 ppm | 21 | 27 | 32 |
| 0.5 ppm | 23 | 45 | 61 |
| 2.0 ppm | 22 | 60 | 80 |
| Lipase isolated from P. sp. | | | |
| 0 ppm | 21 | 27 | 32 |
| 0.5 ppm | 21 | 37 | 46 |
| 2.0 ppm | 20 | 44 | 56 |

As can be seen from the data summarized by Table 1, no oil stain removal is observed in the first cycle, while significant removal is observed in the second and third wash cycles.

Even increasing the enzyme concentration in the wash solution ten-fold to 20 ppm does not provide oil stain removal during initial use in the first cycle as might be expected. Surprisingly, however, the present invention provides significant oil stain removal in subsequent washings, even where no lipase is present in the subsequent wash cycles. This is demonstrated by Table 2.

Four replicate polycotton fabric swatches (2×2") were washed in 200 ml of 10 mM sodium carbonate containing 0.1 mM Neodol 25-9/0.2mM $C_{12}$LAS and various levels of lipase as indicated in Table 2. Wash solutions were at pH 10.5 and washed for 15 minutes at room temperature. Swatches were air dried before rewashing. Rewashing in cycles 2 and 3 were done without the addition of lipase.

TABLE 2

| | Percent Soil Removal | | |
|---|---|---|---|
| | Cycle 1 | Cycle 2 | Cycle 3 |
| Control | 15 | 23 | 27 |
| Enzyme Treated: | | | |
| (2 ppm) | 15 | 57 | 76 |
| (5 ppm) | 17 | 69 | 91 |
| (10 ppm) | 16 | 78 | 101 |
| (20 ppm) | 17 | 89 | 105 |

As is seen by the data of Table 2, polycotton fabric that had been treated with varying concentrations of lipase during the first laundering cycle demonstrated significant oil removal in the second laundering, and even better removal in the third laundering (where only surfactant was present in the second and third launderings). The data of Table 2 further shows that higher enzyme levels in the first cycle resulted in higher levels of oily stain removal in the second and third cycles. This demonstrates that oil removal observed in the second and third cycle is due to the presence of lipase in the first cycle. Furthermore, these data demonstrate that the lipase is adsorbed onto the fabric during cycle 1, and remains active and adsorbed through rinsing, drying, storage and use in cycles 2 and 3.

EXAMPLE 1

An experiment was performed that illustrates the use of lipase compositions to pretreat fabric before the fabric is exposed to oil. Three different enzyme concentrations for Lipase 1 were used to treat three separate sets of polyester/cotton (65/35) fabric swatches. The treatment consisted of washing four replicates in the wash solution described in Table 2 containing various lipases shown in Table 3. After air drying, each swatch was then stained with triolein (5 wt. % with respect to fabric weight). Control (untreated) swatches were similarly stained. The stained swatches were then washed once in a laundering simulation including detergent and the described levels of lipase. Table 3 summarizes the data.

TABLE 3

| | % Stain Removal | | |
|---|---|---|---|
| PreTreatment | (0.5 ppm) | (1.0 ppm) | (2.0 ppm) |
| Control(no lipase) | 6 | 8 | 12 |
| Lipase cloned from *P. putida* | 20 | 26 | 33 |
| Lipase P. sp | 20 | 20 | 26 |
| Novo Lipolase | 9 | 7 | 11 |

As can be seen from the data summarized by Table 3, the fabrics pretreated (pretreated before oil exposure) with lipase cloned from *Pseudomonas putida* and the lipase isolated from Pseudomonas sp. resulted in about 2½ to almost 3 times better oil stain removal with respect to a control when both control and pretreated fabric were washed in a laundry simulation that included detergent and lipase.

The lipase-surface complexes have been shown to exhibit binding tenacity, and to retain activity binding on a broad spectrum of surfaces. This is illustrated in Table 4 where a wide variety of fabrics, several non-fabric woven surfaces, and several solid surfaces were soaked for 15 minutes in a buffered solution of lipase at pH 8. By calculation of the activity lost from solution, the amount of lipase sorbed onto the surfaces was determined. These fabrics and surfaces were then washed for 15 minutes in 5 mM phosphate at pH 8 and the amount of enzyme that had desorbed was similarly measured. Table 4 summarizes these sorption and desorption results.

TABLE 4

| Fabric/ Surface Type | % sorbed from treating solution | % remaining sorbed after one washing |
|---|---|---|
| nylon | 22 | 98 |
| polycotton | 32 | 92 |
| grey polycotton | 13 | 85 |
| polyester | 29 | 96 |
| woven polyester | 27 | 93 |
| double knit polyester | 53 | 97 |
| silk (crepe de chenin) | 8 | 87 |
| vinyl | 16 | 94 |
| cotton flannel | 19 | 93 |
| rayon velvet | 51 | 84 |
| acrylic felt | 38 | 100 |

TABLE 4-continued

| Fabric/ Surface Type | % sorbed from treating solution | % remaining sorbed after one washing |
|---|---|---|
| polyester/wool | 37 | 96 |
| polyester /polyurethane | 8 | 84 |
| terry (85% cotton /15% polyester) | 17 | 97 |
| fleece (50% cotton /50% Polyester) | 39 | 97 |
| nylon pot cleaner | 38 | 71 |
| copper cloth pot cleaner | 42 | 93 |
| cellulose sponge | 24 | 100 |
| stainless pot cleaner | 68 | 99 |
| wax paper | 17 | 99 |
| unetched glass | 39 | 99 |
| etched glass | 33 | 100 |
| ABS pipe | 22 | 1 |

As can be seen from this data, the lipase was sorbed from the treating solution, in varying amounts, depending on the surface, for a variety of different fabrics and surfaces. Furthermore, once sorbed the bound enzyme was substantially retained even after a 15 minute wash in phosphate buffer as described above. Four days after the laundering simulation, the enzyme activity of the surface-bound complexes was tested. All the examples summarized by the data of Table 4 were shown to be hydrolyticly active. This was demonstrated by contacting the lipase treated surfaces with p-nitrophenylbutryate, a substrate for the lipase, that is hydrolyzed to the yellow product p-nitrophenol.

Treating fabrics to improve oil stain removal in accordance with the invention normally begins by contacting the desired fabric with a lipase containing composition to sorb the lipase onto the fabric and to form fabric-lipase complexes. Factors which affect adsorbance of lipase onto surfaces include surface characteristics and solution components such as: surfactant composition, ionic strength, pH, and lipase concentration. The time of exposure of the surface to the lipase-containing solution also increases the amount of adsorbed lipase. We have found that adsorption is highest on polycotton fabric in the absence of surfactant, low ionic strength and alkaline pH. Under these preferred conditions, higher lipase concentrations in solution will provide higher adsorption of the lipase onto the fabric. In the presence of surfactants, mixtures of anionic/nonionic promote adsorption more efficiently than single surfactant systems.

Delivery of the lipase to the surface to form the surface-lipase complex can be effected in a number of ways. As previously discussed, one way is by contacting the surface with a lipase solution, either in by washing or spraying the surface with the solution. An example of a preferred aqueous solution suitable for application to fabric has a basic pH, most preferably pH 10.5, has the lipase preferably in an amount of about 20 ppm, and is buffered such as by 5 mM phosphate or 10 mM carbonate. Simply soaking or spraying such a composition on the fabric surfaces for which improved oil stain removal is desired will result in formation of fabric-lipase complexes with the desired laundering removal resistance and substantial hydrolysis activity already described.

Such delivery may be made prior to soiling, for instance as a finishing step in fabric manufacture, or in pretreatment of fabrics prior to use; or after soiling of the fabric. Localized treatment of oil stains prior to washing can be effected by spraying or by use of a solid or gelled carrier for the lipase in applications where the lipase is desired to be transferred to fabric by direct contact. For example, a consumer can use a gel stick applicator to directly apply the lipase to areas such as shirt collars. Various suitable solid, stick-like carrier compositions are illustrated in European Patent Application No. 86107435.9, published Dec. 30, 1986. For example, one preferred composition includes propylene glycol, nonylphenol ethoxylate, linear alcohol ethoxylate, dodecylbenzenesulfonic acid, and stearic acid. A particularly preferred embodiment for a solid or gelled carrier composition is as follows:

| Component | Weight % |
|---|---|
| Propylene Glycol | 42 |
| Nonylphenol Ethoxylate | 17 |
| Linear Alcohol Ethoxylate | 17 |
| Polyethylene Glycol | 2 |
| Dodecylbenzenesulfonic Acid | 6 |
| Stearic Acid | 10 |
| Lipase | 6 |

Although the reason the lipases of the present invention are not effective when merely added to a conventional laundry wash solution, but are effective when the surface-lipase complex of the present invention is formed, is not fully understood, it is believed, without being bound by this theory, that the structure of these lipases is altered to an active state when they are complexed to the surfaces. Therefore, a method of providing active lipase for use in a conventional laundry solution is also provided by the present invention. This comprises delivery of an article comprising a surface-lipase complex to the conventional wash solution. Such articles can include the lipase complexed with a fabric or non-fabric member. Preferably the non-fabric, particulate members are employed to provide adequate dispersion through the wash. Such particulate members should be hydrophobic surfaces onto which the lipases adsorb. Examples are stearate salts, methacrylate copolymers, hydroxybutylmethyl cellulose, and polyacrylamide resins.

The surface-lipase complex of the present invention preferably has the following characteristics: substantial hydrolysis activity during storage, enhanced stability compared to lipases in solution, and surface property modifications of the surface onto which it is immobilized. The following are examples illustrating these characteristics.

EXAMPLE 2

This example illustrates activity during storage. Polyester/cotton swatches were treated with a lipase containing solution to provide a fabric-lipase complex. The dry, treated swatches were soiled with triolein (5% by weight of fabric) and stored for two days at room temperature. The oil was then extracted from the swatches and the components of the extracted oil were determined by thin layer chromatography. This analysis showed that oleic acid, monoolein and diolein were present on the swatches. These products of lipolytic hydrolysis were not observed on "control swatches" (where there was no enzyme treatment prior to staining). The presence of oleic acid, monoolein, and diolein demonstrates that the fabric-lipase complex, in accordance with the invention, is active for hydrolysis of oily soil even on dry fabric.

EXAMPLE 3

The following experiments demonstrate that the inventive fabric-lipase complex displays enhanced stability towards:

A. High Temperatures

The bound lipase-fabric complexes retain activity despite drying of the laundered fabrics in hot (180° F.) dryers. This is illustrated by the data of Table 6.

TABLE 6

| Drying conditions | % oil removed 3 Cycles |
|---|---|
| Inventive treated fabric - air dried | 82 |
| Inventive treated fabric - hot dryer | 65 |
| Control - air dried | 20 |

As can be seen from the data of Table 6, although fabric dried three times in a hot dryer (following three launderings) did experience some enzyme activity loss with respect to an inventively treated fabric that was air dried, nonetheless oil removal for even the hot dried, inventively treated fabric was still over three times that of a control (untreated) fabric.

B. Surfactants

The lipase-surface complex has been shown to exhibit enhanced stability to denaturation by surfactants. This property can be useful in liquid formulations, for example, in conveying storage stability. Into a solution of surfactant and buffer an aliquot of hydrolase (Lipase 1) was incubated for 10 minutes at room temperature. The surfactant solution was 1 wt. % SDS, which was buffered by sodium carbonate to pH 10.5. The hydrolase was 2 ppm in solution. A second sample was similarly prepared except fabric was introduced into the surfactant/buffer solution before adding the aliquot of hydrolase. Both samples were then assayed for enzyme activity by removing aliquots at 2, 5, and 10 minutes and assaying for enzyme activity. In addition, the fabric from the second sample was removed and the fabric surface was assayed visually for yellow colored development after contacting with PNB.

We found that the first sample enzyme (which was simply in solution and incubated in the surfactant/buffer solution) was inactive at all time points tested. Similarly, the second sample had some enzyme remaining in solution (that had not sorbed to the fabric) and this solubilized hydrolase was also inactivated. But by contrast, assays of the fabric surface showed that the hydrolase having sorbed to the fabric surface remained active at all points of testing, including even after 10 minutes in the otherwise denaturing surfactant/buffer solution.

EXAMPLE 4

We have discovered that surfaces treated with lipase in accordance with the invention also causes a changed wetting characteristics of the surface. This is demonstrated for three surfaces:

A. Polycotton

Figure 2:
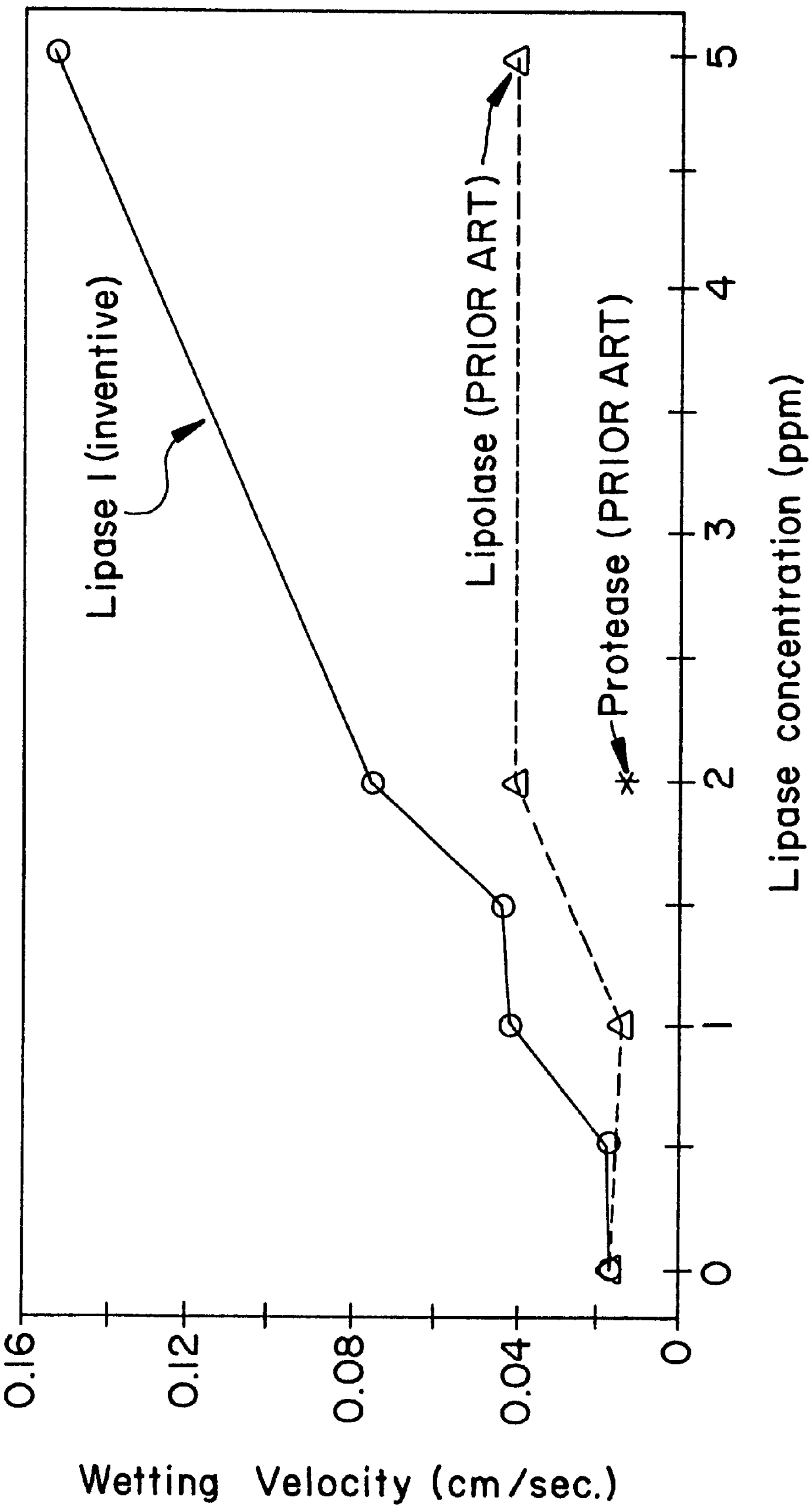
FIG. 2 graphically illustrates the increased wettability of polycotton fabrics when they are treated in accordance with the invention and contrasts this increased wettability with fabric washed in the presence of a prior art, commercially available lipase.

Polycotton fabric treated with the lipases results in increased wetting velocity for that fabric when compared with untreated fabric. FIG. 2 shows the increased wettability of polycotton fabrics when treated in accordance with the invention. The FIG. 2 measurements were made using high speed videomicrography to observe and to measure the behavior of a water droplet as it contacts the fabric surface. The measurement of the contact angle as a function of time (msec) allows calculation of the velocity of wetting. Also shown in FIG. 2 is a comparison with polycotton that had been analogously treated with a commercially available Lipolase enzyme. Within the error of the experiments, the Lipolase enzyme treatment did not affect fabric wettability. A similar result (wettability not affected) was obtained in experiments involving a protease (commercially available as Savinase).

B. ABS Piping

These experiments used sessile drop shape analysis to evaluate the surface properties of ABS plastic pipe. The hydrolase solution used to contact the pipe surface was a solution containing 1 ppm hydrolase. After drying, the contact angle of a water drop as it spread over the pipe surface provided a measurement of the surface hydrophilicity. Table 7 summarizes the data.

TABLE 7

| Treatment | Contact Angle |
|---|---|
| No hydrolase | 66.7 ± 3° |
| Hydrolase | 59.6° |
| | 64.8° |
| | 51.0° |

Three different areas of the pipe were examined to test for homogeneity of sorption. The data suggests that hydrolase sorption was not homogeneous throughout the pipe surface, as can be inferred by the scatter in the contact angle measurements on the hydrolase treated pipe surface. No such scatter was observed on the surface of the untreated pipe. However, all three areas showed a lower contact angle with sorbed hydrolase. This lower contact angle indicates that the surface having sorbed hydrolase had become more hydrophilic and therefore was more easily wetted by water. This surface modification may provide preventative maintenance for drainage pipes.

C. Glass

Glass slides were also studied for sorption. Three compositions were prepared. The first composition was a control aqueous solution with 50 mM $HPO_4^{--}$ buffer (pH 8.0). The second was a surface modifying composition of the invention to which 0.2 ppm lipase (isolated from a clone of *P. putida* organism) was added to the buffered control. The third composition was analogous to the second, but included 10 ppm of the lipase. The glass slides were soaked in one of the respective solutions for one hour, dried, and then the contact angle of a water drop as it spread over the glass slide surface was measured to indicate surface hydrophilicity. The slide soaked in the control solution had a contact angle of 53°, that soaked in the 0.2 ppm lipase composition had a contact angle of 44°, and that soaked in the 10 ppm lipase composition had a contact angle of 30°. These lower contact angles for glass surfaces treated in accordance with the invention indicate that the glass surfaces having sorbed hydrolase had become more hydrophilic and therefore the treated surfaces were more easily wetted by water. This characteristic may facilitate cleaning of surfaces such as floors, walls, tiles, mirrors, and window glass.

EXAMPLE 5

The fabric-lipase complex has also been shown to be effective in preventing redeposition of oily soils onto treated fabric surfaces. This is illustrated in this example.

Removal of oily soil from one fabric only to redeposit that oil (or its hydrolyzed derivatives) onto another, unsoiled fabric during the wash is a particular problem in laundry containing mixed fabric types. Lipase 1 was shown to be useful as an anti-redeposition agent by the following example. 2" by 2" 100% cotton swatches were soiled with 95 mg of triolein. Two of these soiled swatches were then washed along with two clean polyester swatches (2" by 2") in a surfactant solution (0.3 mM $C_{12}$LAS/Neodol 25-9, 2:1 molar ratio) at pH 10.5 (buffered with 10 mM $Na_2CO_3$). The washes were at room temperature (25° C.) for a duration of 15 minutes. These swatches were then dried and oils on the swatches were measured gravimetrically by removing oil from the fabric with a solvent, evaporating the solvent, and weighing remaining oil. Following this procedure, the cotton swatches (originally soiled with 95 mg of triolein) retained 17 mg of triolein but the initially oil-free polyester swatches were found to have had 35 mg of triolein deposited onto them during the washing with soiled cotton swatches.

Two fabric treating methods using Lipase 1 were conducted. In the first fabric treating procedure the clean polyester swatches were pretreated with hydrolase by washing the clean polyester swatches in the above-described surfactant/carbonate solution but where the solution had added 1 ppm Lipase 1. After drying the clean polyester swatches were again washed in the presence of the oil stained cotton swatches as already described.

Another treatment procedure was where the 1 ppm Lipase 1 was simply added ("in situ") to the surfactant/carbonate wash while the oil stained cotton swatches were being washed along with the initially cleaned polyester swatches.

Table 8 demonstrates the control (no hydrolase treatment), the pretreatment, and the in situ treatment data following the procedures as have been just described.

TABLE 8

| Hydrolase Treatment of Polyester Swatches | Cotton Swatch Oil Level Before Lauder-ing | Cotton Swatch Oil Level After Redeposition Laundering | Polyester Swatch Oil Level Before Laundering | Polyester Swatch Oil Level After Redeposition Laundering |
|---|---|---|---|---|
| None (control) | 95 mg | 17 mg | 0 mg | 34 mg |
| Pretreatment (1 ppm) | 95 mg | 17 mg | 0 mg | 2 mg |
| In situ (1 ppm) | 95 mg | 18 mg | 0 mg | 11 mg |

As can be seen from the data of Table 8, treating the polyester swatches so as to sorb the hydrolase onto their surfaces before exposure to potentially redepositing oil (from the soiled cotton swatches) was effective to prevent most of the redeposition when the polyester swatches had already been treated, and substantially reduced the amount of oil redepositing when the treatment was in situ. This experiment demonstrates the efficacy of Lipase 1 as an anti-redeposition agent.

Effective surface modifying compositions of the invention preferably have enzyme within the range of 0.1 g/ml enzyme (0.1 ppm) and 20 g/ml enzyme. Of course, yet higher concentrations could be used. Efficacy of the lipase even when only 0.1 ppm lipase compositions are used for fabric treating is shown by the data in Table 9.

TABLE 9

| | % of oil stain removed | |
|---|---|---|
| | 2 Cycles | 5 Cycles |
| fabric treated with lipase at 0.1 μg/ml (invention) | 30 | 44 |
| control | 24 | 29 |

As can be seen from the data summarized in Table 9, even the very small amount of lipase (isolated from a clone of the *P. putida*) used in a treatment in accordance with the invention results in a statistically significant oil removal benefit for the fabric after two laundering cycles with respect to an untreated control. Indeed, the benefit increases upon multiple cycles and results in almost a 50% increase over the control (untreated fabric) after five laundering cycles.

In another aspect of the present invention a concentrated delivery system useful for generating a bleaching agent comprises a vessel, a surface structure disposed within the vessel, a lipase adjacent to or carried by said surface structure, and means for admitting a selected amount of oil and a selected amount of peroxygen to said vessel and into contact with said surface structure for generation of a peracid within the vessel via enzymatic catalysis. For example, for home laundering an embodiment of the inventive apparatus can serve both to generate a bleaching agent within the limited volume of the vessel as well as to dispense the bleaching agent generated into the laundering solution. A porous vessel can have lipase immobilized within the vessel interior. The lipase is preferably immobilized within the vessel interior, such as on a wall forming at least part of the vessel interior or a member defining a surface within the vessel, by both covalent and noncovalent coupling. Covalent coupling may be by various conventional means known to the art, such as through the N-terminal amine as is used for coupling antibody to membranes.

Figure 3:
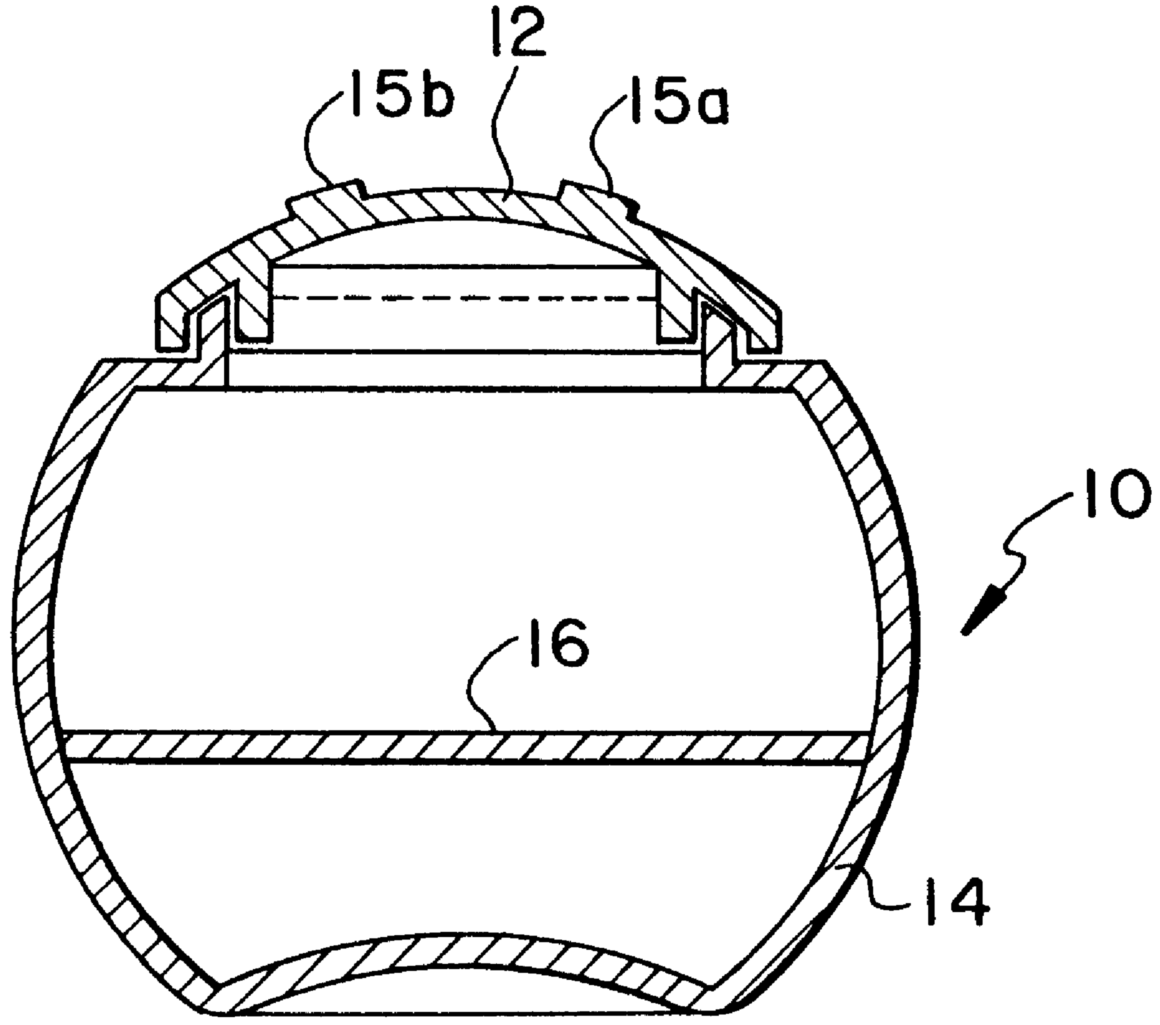
FIG. 3 is a sectional view of a vessel useful for generating a bleaching agent in accordance with the present invention.

Referring to FIG. 3, a generally spherical vessel 10 has a cover assembly 12 and a body 14. Cover assembly 12 is fixed in a removable manner on body 14, such as by a rotary-type mounting, or "twist-off" or any other quick and releasable mountings known to the art. Cover assembly 12 preferably includes a plurality of vents 15*a, b*. Body 14 has a surface structure 16 exposed to the interior on which lipase is immobilized (not illustrated). This structure 16 can take a wide variety of forms. In use, when the cover assembly 12 is removed, then the body 14 has the selected amounts of oil and of peroxygen added to a level sufficient to contact surface structure 16 with its immobilized enzyme for generation of peracid within the vessel 10. As earlier noted, the immobilized enzyme is preferably bound to the structure 16 by both covalent and noncovalent coupling.

Noncovalent coupling is believed involved in forming enzyme-surface complexes through enzyme sorption as has earlier been described. When the consumer adds a selected amount of oil and a selected amount of peroxygen to the vessel interior and into contact with the immobilized lipase, then the lipase, its substrate, and the peroxygen will react to produce peracid in the limited volume of the vessel when in the presence of a substrate-solubilizing aqueous solution, such as a laundering composition. This is because a lipase, such as Lipase 1, will perhydrolyze substrates such as glycerides, ethylene glycol derivatives, or propylene glycol derivatives, which, in the presence of a source of hydrogen peroxide, will form peracid. Such peracid bleaching systems utilizing these three essential components are more fully described in Ser. No. 932,717, filed Nov. 19, 1986, titled “Enzymatic Peracid Bleaching System,” of common assignment herewith and incorporated hereby by reference. Example 6 illustrates this bleaching agent generation apparatus aspect of the invention.

EXAMPLE 6

A protocol was devised to determine whether a peracid (such as peroctanoic acid) in reasonably high concentrations could be generated using a lipase in a limited volume device that would be added to the wash when one desired laundry bleaching.

We prepared a surface structure with immobilized enzyme by pipetting 0.8 ml of 6.6 g/l lipase solution (isolated from a clone of the *P. putida* organism) into a weigh boat, added a fabric swatch and soaked the swatch in the solution overnight. The swatch was then treated by rinsing in sodium carbonate buffer at pH 11 for fifteen minutes with two water rinses to remove unbonded enzyme. This swatch, or surface structure with lipase carried on the surface, then was placed into contact with a selected amount of substrate for the lipase and a selected amount of peroxygen within a limited volume (a beaker). The substrate was 0.1 weight percent trioctanoin (in 200 ml, 0.2 g trioctanoin). The peroxygen was hydrogen peroxide (5000 ppm A.O. by calculation 6.5 ml/200 ml). Both the substrate (oil) and peroxygen were in an aqueous solution buffered with sodium carbonate (25 mM) to pH 10.8 with EDTA 0.2 ml/200 ml (50 $\mu$M). Liquid chromatography (Brinkman autoanalyzer) was used to determine the amount of peracid generated as a time function, as illustrated by Table 10.

TABLE 10

| Elapsed Time (min) | ppm A.O. generated |
|---|---|
| 6 | 4.8 |
| 12 | 7.8 |
| 18 | 8.8 |
| 25 | 9.3 |

A control (with no enzyme present) resulted in the generation of 0.05 ppm A.O. in 12 minutes. Thus, while only an insignificant amount of chemical perhydrolysis (between substrate and peroxygen) occurred, the immobilized enzyme placed into contact with substrate and peroxygen generated peracid within the vessel via enzymatic catalysis.

Another composition was prepared in which the substrate oil was increased to 52 g/200 ml. EDTA was present as 0.6 ml in 600 ml, there was 2% PVA, and the solution was prepared with 350 ml water. The hydrogen peroxide was also increased (10 ml into 150 ml emulsion sample) and the initial pH of the emulsion was raised (using 50% NaOH) to 10.8. The enzyme amount was 6.8 mg/swatch which is equivalent to about .1 ppm in a 70 liter wash. The amount of available oxygen generated for this system was again calculated and the results are shown as is shown in Table 11.

TABLE 11

| Elapsed Time (min) | ppm A.O. generated |
|---|---|
| 1 | 175 |
| 4 | 390 |
| 7 | 360 |
| 10 | 340 |
| 14 | 404 |

A control with no immobilized enzyme resulted in no peracid being detected after 14 minutes. These experiments indicate that peroctanoic acid at high concentrations (30 mM) can be generated by immobilizing a lipase in accordance with the invention and employing the immobilized enzyme as a catalyst for a reaction system with hydrogen peroxide (2%) and oil substrate trioctanoin (8.7% g/100 ml).

It is to be understood that while the invention has been described above in conjunction with preferred specific embodiments, the description and examples are intended to illustrate and not limit the scope of the invention, which is defined by the scope of the appended claims.

| | | | | | | | | | | | |
|---|---|---|---|---|---|---|---|---|---|---|---|
| 1 | | | | | | | | | 10 | | |
| ala | pro | leu | pro | asp | thr | pro | gly | ala | pro | phe | pro |
| | | | | | | | 20 | | | | |
| ala | val | ala | asn | phe | asp | arg | ser | gly | pro | tyr | thr |
| | | | | | 30 | | | | | | |
| thr | ser | ser | gln | ser | glu | gly | pro | ser | cys | arg | ile |
| | | | 40 | | | | | | | | |
| tyr | arg | pro | arg | asp | leu | gly | gln | gly | gly | val | arg |
| | 50 | | | | | | | | | | 60 |
| his | pro | val | ile | leu | trp | gly | asn | gly | thr | gly | ala |
| | | | | | | | | | 70 | | |
| gly | pro | ser | thr | tyr | ala | gly | leu | leu | ser | his | trp |
| | | | | | | | 80 | | | | |
| ala | ser | his | gly | phe | val | val | ala | ala | ala | glu | thr |
| | | | | | 90 | | | | | | |
| ser | asn | ala | gly | thr | gly | arg | glu | met | leu | ala | cys |
| | | | 100 | | | | | | | | |
| leu | asp | tyr | leu | val | arg | glu | asn | asp | thr | pro | tyr |
| | 110 | | | | | | | | | | 120 |
| gly | thr | tyr | ser | gly | lys | leu | asn | thr | gly | arg | val |
| | | | | | | | | | 130 | | |
| gly | thr | ser | gly | his | ser | gln | gly | gly | gly | gly | |
| | | | | | | | 140 | | | | |
| ile | met | ala | gly | gln | asp | thr | arg | val | arg | thr | thr |

-continued

| | | | | | | | | | | | |
|---|---|---|---|---|---|---|---|---|---|---|---|
| | | | | | 150 | | | | | | |
| ala | pro | ile | gln | pro | tyr | thr | leu | gly | leu | gly | his |
| | | | 160 | | | | | | | | |
| asp | ser | ala | ser | gln | arg | arg | gln | gln | gly | pro | met |
| | 170 | | | | | | | | | | 180 |
| phe | leu | met | ser | gly | gly | gly | asp | thr | ile | ala | phe |
| | | | | | | | | | 190 | | |
| pro | tyr | leu | asn | ala | gln | pro | val | tyr | arg | arg | ala |
| | | | | | | | 200 | | | | |
| asn | val | pro | val | phe | trp | gly | glu | arg | arg | tyr | val |
| | | | | | 210 | | | | | | |
| ser | his | phe | glu | pro | val | gly | ser | gly | gly | ala | tyr |
| | | | 220 | | | | | | | | |
| arg | gly | pro | ser | thr | ala | trp | phe | arg | phe | gln | leu |
| | 230 | | | | | | | | | | 240 |
| met | asp | asp | gln | asp | ala | arg | ala | thr | phe | tyr | gly |
| | | | | | | | | | 250 | | |
| ala | gln | cys | ser | leu | cys | thr | ser | leu | leu | trp | |
| ser | val | glu | arg | arg | gly | leu | | | | | |

What is claimed is:

1. A treated fabric having improved oil stain removal, consisting essentially of:

a fabric; and a lipase sorbed on the fabric surface, the lipase being isolatable from a Pseudomonas organism.

2. The treated fabric as in claim 1 wherein the sorbed lipase forms fabric-lipase complexes having substantial hydrolysis activity for oil stains.

3. The treated fabric as in claim 1 or 2 wherein the sorbed lipase alters the wettability of the fabric surface.

4. The treated fabric as in claim 1 or 2 wherein the lipase is isolated from an organism expressing a coding region found in or cloned from *Pseudomonas putida* ATCC 53552, the lipase having a molecular weight of about 30 to 35 kd and being resolvable as a single band by SDS gel electrophoresis.

5. The treated fabric as in claim 4 wherein the. sorbed lipase retards redeposition of oil and hydrolysis by-products during oil removal from the surface in the presence of aqueous solutions.

6. The treated fabric as in claim 2 wherein the sorbed lipase retains at least some hydrolysis activity when the fabric is exposed to drying at elevated temperatures.

7. The treated fabric as in claim 4 wherein the sorbed lipase is resistant to removal during laundering of the fabric.

8. The treated fabric as in claim 4 wherein the sorbed lipase alters the wettability of the fabric.

9. A method for modifying surfaces to facilitate oil removal, consisting essentially of:

selecting a surface to be modified;

immobilizing a lipase onto the surface, the lipase being isolatable from a Pseudomonas organism.

10. The method as in claim 9 wherein the lipase is isolated from an organism expressing a coding region found in or cloned from *Pseudomonas putida* ATCC 53552 or genetic mutants thereof, the lipase having a molecular weight of about 30 to 35 kd and being resolvable as a single band by SDS gel electrophoresis.

11. The method as in claim 9, wherein the immobilized lipase forms surface-lipase complexes on the surface having substantial hydrolysis activity for oil stains.

12. The method as in claim 11 wherein the immobilized lipase forms surface-lipase complexes on the surface having enhanced stability to denaturation by surfactants and to heat deactivation.

13. A method of treating fabric to improve oil stain removal, consisting essentially of:

selecting a fabric to be modified;

sorbing a lipase onto the fabric, the lipase being isolatable from a Pseudomonas organism.

14. The method as in claim 13 wherein the sorbed lipase forms fabric-lipase complexes having substantial hydrolysis activity for oil stains on the fabric while in the presence of air.

15. The method as in claim 13 or 14 wherein the lipase is isolated from an organism expressing a coding region found in or cloned from *Pseudomonas putida* ATCC 53552, the lipase having a molecular weight of about 30 to 35 kd and being resolvable as a single band by SDS gel electrophoresis.

16. The method as in claim 15 wherein the sorbed lipase retards redeposition of oil and hydrolysis by-products during laundering of the fabric.

17. The method as in claim 15 wherein the sorbed lipase retains at least some hydrolysis activity when the fabric is exposed to drying at elevated temperatures.

18. The method as in claim 15 wherein the sorbed lipase is resistant to removal during laundering of the fabric.

19. The method as in claim 15 wherein the sorbed lipase alters the wettability of the fabric.

20. The method as in claim 14 wherein at least some of the hydrolysis by-products are removable during laundering of the fabric at basic pH or in the presence of surfactant.

21. The method as in claim 14 wherein at least most of oil stains when present on the fabric are removed via hydrolysis by-products after three launderings.

22. The method as in claim 15 wherein the lipase is sorbed by contacting the fabric with an lipase containing composition having the lipase in an amount between about 0.1 ppm to about 2,000 ppm.

* * * * *